United States Patent [19]

Diehl

[11] Patent Number: 4,770,705
[45] Date of Patent: Sep. 13, 1988

[54] SALTS OF ALKYL-2-BENZIMIDAZOLE-CARBAMATE AND FUNGICIDAL COMPOSITIONS THEREOF SUITABLE FOR PAINTS AND PLASTER

[75] Inventor: Karl-Heinz Diehl, Norderstedt, Fed. Rep. of Germany

[73] Assignee: Schulke & Mayr GmbH, Norderstedt, Fed. Rep. of Germany

[21] Appl. No.: 942,230

[22] Filed: Dec. 16, 1986

[51] Int. Cl.⁴ .................. C09D 5/16; A01N 43/52; A61K 31/415; C07D 235/32
[52] U.S. Cl. ..................... 106/18.32; 71/67; 514/395; 548/329
[58] Field of Search ............. 548/329; 514/395; 71/67; 106/18.32

[56] References Cited

U.S. PATENT DOCUMENTS 4,046,906  9/1977  Frensch et al. .............. 548/329

Primary Examiner—John M. Ford
Assistant Examiner—Northington, Zinna
Attorney, Agent, or Firm—Cushman, Darby & Cushman

[57] ABSTRACT

A water insoluble compound of formula I

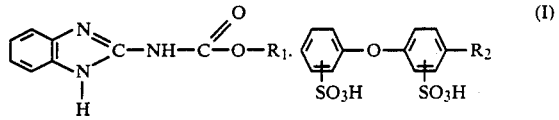

wherein $R_1$ is an alkyl group having 1 to 4 carbon atoms and $R_2$ is a straight-chain or branched-chain alkyl group having from 10 to 16 carbon atoms. The compounds of the present invention are useful in fungicidal compositions suitable for combatting fungus in plaster and paint.

9 Claims, No Drawings

SALTS OF ALKYL-2-BENZIMIDAZOLE-CARBAMATE AND FUNGICIDAL COMPOSITIONS THEREOF SUITABLE FOR PAINTS AND PLASTER

The present invention relates to salts of alkyl-2-benzimidazole carbamates, fungicidal compositions containing said salts and a process for combatting fungus and algae in paint and plaster coatings.

Salts of benzimidazole-carbamic acid esters, also known as 2-(methoxy-carbonylamino)-benzimidazole (BCM) are known to have some fungicidal effect. Further, salts of BCM with an acid having an ionization constant of more than $1 \times 10^{-5}$ are known as fungicides (British Specification No. 1,195,180). These salts are applied in the form of an aqueous solution when used for combatting fungal diseases in plants. A serious drawback of these salts, however, is the fact that they undergo hydrolysis in aqueous solutions. The free benzimidazole-carbamate precipitates in the form of crystals resulting in a reduction of fungicidal activity.

Adducts of salts of benzimidazole-carbamic acid esters and organic sulfonic and sulfuric acids are known from U.S. Pat. No. 4,046,906 as is their use in fungicidal compositions for combatting fungal diseases in plants. Although these compounds are suitable for the production of ultra low volume formulations in organic solvents, aqueous solutions of these compounds are unsuitable since evaporation of the water during application, e.g. by spray-drying, would result in the dry salts being lost in the wind.

It is an object of the present invention to provide new salts of alkyl-2-benzimidazole-carbamates which are practically insoluble in water but which are stable and have excellent properties for being formulated into emulsions or dispersions.

It is a further object of the present invention to provide a fungicidal composition containing new salts of alkyl-2-benzimidazole-carbamates which are particularly suitable for combatting fungus in plaster and paint.

A still further object of the present invention is to provide a fungicidal composition as above having in addition thereto one or more biocidal, especially algicidal components which synergistically improve the resistance of plaster coated walls and paint to the attack of fungus and algae.

The foregoing objects of the invention are achieved by adducts or salts of benzimidazole-carbamic acid esters and special organic disulfonic acids, said salts or adducts having the general formula:

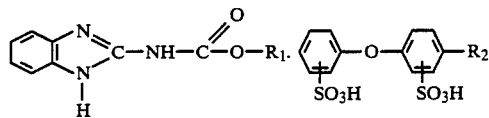

(I)

wherein $R_1$ is an alkyl group having 1 to 4 carbon atoms and $R_2$ is an alkyl group having 10 to 16 carbon atoms, preferably a $C_{12}$ branched-chain alkyl group derived from polypropylene.

Surprisingly, it has been found that when alkyldiphenyloxide-disulfonic acids (ADOD) are used for the formation of salt with the alkyl-2-benzimidazole-carbamates (BCM), the water solubility of the adducts is markedly reduced while the availability of the fungicides on substrates such as paint or plaster is not diminished. The reduced water solubility is particularly advantageous when paint and plaster containing the active ingredients are applied to surfaces such as outside walls, since loss of the compounds to rain and wind is markedly reduced.

Surprisingly, it has also been found that the shelf life of paints containing the fungicidal compositions of the present invention is markedly increased.

In the present invention the alkyl-2-benzimidazole-carbamate or the 2-(alkoxycarbonylamino)-benzimidazole may have alkyl groups with 1 to 4 carbon atoms such as methyl, ethyl, propyl, isopropyl, butyl or isobutyl, preferably a methyl group.

The alkyldiphenyloxide-disulfonic acids may have alkyl groups of 10 to 16 carbon atoms. The preferred alkyl group is branched-chain and has 12 carbon atoms such as those derived from tetrapropylene.

The BCM salts with the alkyldiphenyloxide-disulfonic acids according to the present invention can be used as a fungicidal composition in pulverized form containing 2 to 95% by weight of the compound of the invention, preferably 65 to 95% by weight. The remaining components are inert carriers such as talcum, bentonite or clay or other usual additives such as dispersants or wetting agents, non-ionic surface active agents are preferred.

The fungicidal compositions may also be used in the form of a solution or emulsion containing the active ingredients in the amount of 5 to 30% by weight.

An effective amount of biocidal, especially algicidal compounds may be added to the fungicidal compositions in an amount of 200% by weight or more based on the weight of the BCM compound. The following compounds are preferred: tetramethylthioramdisulfide, N-trichloromethylthiophthalimide, 1-butyl-(carbamoyl)-2-benzimidazole-carbamic acid methyl ester, 2-rhodane methylthiobenzthiazole, 2-(thiazolyl-(4))-benzimidazole, dodecylguanidinoacetate, N-dichlorofluoromethylthio-N',N'-di-methyl-N-phenylsulfuric acid diamide, 2-cyano-N-(ethylaminocarbonyl)-2-(methoxyimino)-acetamide, N-(n-propyl)-N-(2,4,6-trichlorophenoxyethyl)-N'-imidazolyl-urea, 3-(3,4-dichlorophenyl)-1,1-dimethyl-urea, 2-methylthio-4-t.-butylamino-6-cyclopropylamino-s.-triazine, 2-n-octyl-4-isothiazoline-3-on, 2-cyclohexyl-4-isothiazoline-3-on, 2-dodecyl-4-isothiazoline-3-on, 2-benzyl-4-isothiazoline-3-on and dithiocarbamates and their derivatives such as Maneb and ZiLneb which are generic names for the manganese and zinc salts of dithiocarbamates.

The following examples are provided for the purpose of describing the preparation of compounds and compositions of the present invention and for illustrating the advantages thereof. It should, however, be understood that these examples are for illustrative purposes only and are by no means to be considered as limiting.

EXAMPLES OF PREPARATION

Example 1

Dodecyldiphenyloxide-disulfonic acid adduct of 2-methoxycarbonylaminobenzimidazole (BCM).

Eighty grams of 2-methoxycarbonylaminobenzimidazole and 270 grams of a 40% dodecyldiphenyloxide-disulfonic acid were added with stirring to 645 grams of 1,2-propylene glycol. Stirring was continued while heating the reaction mixture to a temperature of 80° C., which temperature was maintained for 4 hours. Thereafter, the reaction mixture was cooled and the precipitated salt of the disulfonic acid and BCM was isolated and dried. The crude product has a decomposition point of 92°–113° C. and was in the form of yellow-whitish crystals having a water solubility of less than 0.001%. That the structure was that given in formula I was confirmed by thin layer chromatography and NMR spectroscopy.

The dodecyldiphenyloxide-disulfonic acid used in the above Example was a dark liquid having an average molecular weight of 524 being sold as DOWFAX 2AO by The Dow Chemical Company.

Example 2

Four grams of 2-methoxycarbonylaminobenzimidazole were added dropwise to 64.5 grams of 1,2-propylene glycol. After the addition of 13.5 grams of a 40% dodecyldiphenyloxide-disulfonic acid the whole mixture was stirred for a period of 3 hours at a temperature of 75° to 80° C. After cooling below 30° C., 17 grams of N-octylisothiazolinone and 0.5 gram of a mixture of chloromethylisothiazolinone and methylisothiazolinone were added.

EXAMPLES OF FORMULATION

Example A

A fungicidal formulation was prepared by adding 70 grams of the product according to Example 1 to a mixture of 70 grams of 1,2-propylene glycol, 100 grams of ethanol and 60 grams of n-propylalcohol. The mixture was a very effective fungicidal concentrate which can be used in a dispersion in an acrylic paint.

Example B

A solution similar to that of Example A was prepared by adding 22 grams of the product according to Example 2 to 78 grams of a 1:1 mixture of propylalcohol and water. This concentrate was effective at 0.1% by weight in a plaster slurry, for coating outside walls of a hospital.

EXAMPLES OF BIOLOGICAL TESTS

Test Method A

The biological effectiveness of a product according to Example 1 was tested both in an aqueous acrylate paint and in an aqueous plaster dispersion as follows:

To 50 grams of a usual acrylic paint (for composition see Table I) and of a plaster (for composition see Table II) composition to be tested, the fungicidal compound of Example 1 was added in different concentrations. After extensive stirring, the samples were coated on a sheet of pasteboard and dried for 24 hours at room temperature and for an additional 24 hours at 40° C. These paper samples were then subjected for 72 hours to a water sprayout test whereby 1 liter of water per minute was flushed over the paper supports. After drying for 24 hours at room temperature and for 24 hours at 40° C., the test samples were irradiated for 24 hours with ultraviolet light. Test discs having a diameter of 50 mm were cut from the pasteboard and sterilized with ethylene oxide.

Sabouraud-plates were seeded with a 0.2 ml suspension of either *Aspergillus niger* or Alternaria containing about $10^7$ germs per ml. The test discs were put onto the plates and incubated at a temperature of 25° to 27° C. for a period of 3 weeks. After a period of 1 or 2 or 3 weeks, respectively, the contamination was rated as follows:

0 = no fungus formation
1 = very small fungus formation (0–5% of the entire surface)
2 = weak fungus formation (5–25% of the entire surface)
3 = medium fungus formation (25 to 50% of the entire surface)
4 = strong fungus formation (50–99% of the entire surface)
5 = no inhibition of fungus formation.

The results are summarized in Table III. A known tetradecane-sulfonic acid adduct of 2-methoxycarbonylaminobenzimidazole (BCM), CARBENDASULF (Hoechst AG, Frankfurt/Main, Germany; prepared according to Example 1 of U.S. Pat. No. 4,046,906), was used for comparison.

TABLE I

| Paint Composition | |
|---|---|
| Component | Conc % w/w |
| 2,2,4-Trimethyl-1,3-pentanediolmonoisobutyrate | 1.20 |
| Oxyethylcellulose | 0.30 |
| Polymetaphosphate | 0.20 |
| Polyacrylic acid ammonia salt | 0.25 |
| Defoaming agent | 0.92 |
| Ammonia, 25% | 0.05 |
| Titanium dioxide | 20.00 |
| Calciumcarbonate | 10.00 |
| Crystalline calcite | 10.40 |
| Aluminum silicate | 2.00 |
| Acrylic dispersion (50%) | 35.00 |
| Water ad | 100 |

TABLE II

| Component | Conc % w/w |
|---|---|
| Water | 8.640 |
| Hydroxypropylmethylcellulose | 0.097 |
| Bentonite | 0.146 |
| Polymetaphosphate | 0.486 |
| Polyacrylic acid sodium salt | 0.243 |
| Ammonia | 0.097 |
| Defoaming agent | 0.194 |
| Mixture of aliphatic and aromatic hydrocarbon solvents | 1.165 |
| Styrene-maleic acid copolymer | 13.107 |
| Titandioxide | 3.641 |
| Calciumcarbonate | 29.126 |
| Flintstein (special $SiO_2$) | 16.990 |
| Calciumcarbonate | 14.563 |
| Calciumcarbonate | 10.922 |
| Cellulose | 0.486 |
| Defoaming agent | 0.097 |

TABLE III

| Acrylic dispersion paint | Conc. % | *Aspergillus niger* 1 | 2 | 3 | Alternaria 1 | 2 | 3 |
|---|---|---|---|---|---|---|---|
| Control | — | 5 | — | — | 5 | — | — |
| Example 1 | 0.01 | 1 | 2 | 2 | 1 | 2 | 3 |
|  | 0.02 | 1 | 1 | 2 | 1 | 1 | 2 |
|  | 0.05 | 0 | 0 | 0 | 0 | 0 | 0 |
| CARBENDA-SULF | 0.01 | 3 | 3 | 4 | 3 | 3 | 4 |
|  | 0.02 | 2 | 2 | 3 | 2 | 2 | 3 |
|  | 0.05 | 1 | 1 | 2 | 1 | 2 | 2 |
| Plaster |  |  |  |  |  |  |  |
| Control | — | 5 | — | — | 5 | — | — |
| Example 1 | 0.01 | 1 | 2 | 2 | 1 | 2 | 2 |
|  | 0.02 | 0 | 1 | 1 | 0 | 1 | 1 |
|  | 0.05 | 0 | 0 | 0 | 0 | 0 | 1 |
| CARBENDA-SULF | 0.01 | 2 | 3 | 3 | 2 | 3 | 4 |
|  | 0.02 | 1 | 2 | 3 | 1 | 2 | 4 |

TABLE III-continued

| Acrylic dispersion | Conc. % | Aspergillus niger | | | Alternaria | | |
|---|---|---|---|---|---|---|---|
| | | 1 | 2 | 3 | 1 | 2 | 3 |
| | 0.05 | 1 | 1 | 2 | 1 | 2 | 2 |

Test Method B

The product of Example 2 was tested in comparison with the known products X-1 and X-2.

Comparative product X-1 was obtained by adding 4 grams of BCM and 6.5 grams of 98% dodecylarylsulfonic acid to 89.5 grams of 1,2-propylene glycol. The alkylarylsulfonic acid is one the best compounds for forming adducts with BCM according to U.S. Pat. No. 4,046,906. The mixture was stirred for 3 hours at 75° to 80° C. and then cooled.

The other comparative product, X-2, is an effective algicidal composition, namely a mixture of 17 grams of N-octylisothiazolinone in 83 grams of 1.2-propylene glycol.

As in Test Method A, fifty grams of the substrate (compositions of paint and plaster described in Tables I and II, respectively) to be tested were mixed with different concentrations of the product of Example 2 or the comparative products X-1 and X-2.

The test organism used was *Chlorella pyrenoidosa*. Plates with a nutritious coating were seeded with a 0.1 ml suspension of the algae. The plates were covered with paper samples 50 mm in diameter prepared as in Test Method A including the 72 hour flushing with water. An additional 0.3 to 0.5 ml suspension of an algae was added to the surface of the samples. The samples were incubated to 25° to 27° C. under intensive irradiation in a humid atmosphere. After one week, the area of inhibition was rated as follows:

− = no growth
+ = small growth
+ + = moderate growth
+ + + = strong growth.

The values obtained by these tests are summarized in Table IV.

TABLE IV

| | Conc. % | Inhibition area in mm$^2$ | | Rating of Growth |
|---|---|---|---|---|
| Plaster | | | | |
| Example 2 | 0.025 | 7 | 6 | − |
| | 0.05 | 15 | 14 | − |
| Product X-1 | 0.025 | 0 | 0 | +++ |
| | 0.05 | 0 | 0 | +++ |
| Product X-2 | 0.025 | 3 | 2 | + |
| | 0.05 | 11 | 11 | − |
| Acrylate Paint | | | | |
| Example 2 | 0.025 | 7 | 8 | − |
| | 0.05 | 16 | 16 | − |
| Product X-1 | 0.025 | 0 | 0 | +++ |
| | 0.05 | 0 | 0 | +++ |
| Product X-2 | 0.025 | 2 | 2 | + |
| | 0.05 | 8 | 9 | − |

The data in Table IV clearly show that the composition according to the invention (Example 2) has a more pronounced algicidal effect than the best fungicidal composition of U.S. Pat. No. 4,046,906 (X-1) and also shows a better inhibition of growth than does a typical algicide such as N-octylisothiazolinone (X-2).

What is claimed is:

1. A water insoluble compound of formula I

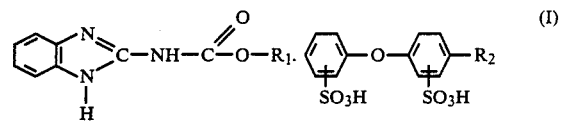

wherein $R_1$ is an alkyl group having 1 to 4 carbon atoms and $R_2$ is a straight-chain or branched-chain alkyl group having from 10 to 16 carbon atoms.

2. A water insoluble compound according to claim 1 wherein $R_1$ is a methyl group.

3. A water insoluble compound according to claim 1 wherein $R_2$ is a branched-chain alkyl group with 12 carbon atoms derived from tetrapropylene.

4. A fungicidal composition comprising a suitable inert carrier and an effective amount of said water insoluble compound of formula I according to claim 1.

5. A fungicidal composition according to claim 4 wherein said composition comprises 2 to 95% by weight of said water insoluble compound of formula I.

6. A fungicidal composition according to claim 4 wherein said composition is an emulsion concentrate containing 5 to 30% by weight of said water insoluble compound of formula I.

7. A fungicidal composition according to claim 4 wherein said composition contains an algicide.

8. A method for combatting fungus in paint and plaster which comprises applying to painted surfaces or plaster surfaces an effective amount of a water insoluble compound of formula I

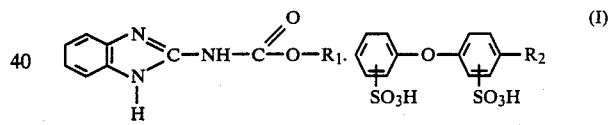

wherein $R_1$ is an alkyl group having 1 to 4 carbon atoms and $R_2$ is a straight-chain or branched-chain alkyl group having from 10 to 16 carbon atoms.

9. A method for combatting fungus and algae in paint and plaster comprising adding to said paint and said plaster an effective amount of a fungicidal composition comprising a suitable inert carrier and an effective amount of a water insoluble compound of formula I

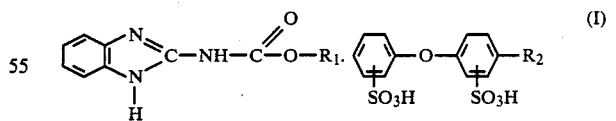

wherein $R_1$ is an alkyl group having 1 to 4 carbon atoms and $R_2$ is a straight-chain or branched-chain alkyl group having from 10 to 16 carbon atoms,
which composition contains an algicide.

* * * * *